United States Patent
Auberson et al.

(10) Patent No.: US 7,655,686 B2
(45) Date of Patent: Feb. 2, 2010

(54) CERTAIN SUBSTITUTED SPIROCYCLIC LACTAMS AND USE THEREOF AS PHARMACEUTICALS

(75) Inventors: Yves Auberson, Allschwil (CH); Ralf Glatthar, Bad Sackingen (DE); Rhys Salter, Basel (CH); Oliver Simic, Basel (CH); Marina Tintelnot-Blomley, Maulburg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/823,311

(22) Filed: Jun. 26, 2007

(65) Prior Publication Data

US 2007/0265328 A1    Nov. 15, 2007

Related U.S. Application Data

(63) Continuation of application No. 10/574,536, filed as application No. PCT/EP2004/011054 on Apr. 10, 2004, now abandoned.

(30) Foreign Application Priority Data

Oct. 3, 2003    (GB) .................................. 0323204.8

(51) Int. Cl.
*A61K 31/407* (2006.01)
*C07D 487/10* (2006.01)

(52) U.S. Cl. ........................ 514/409; 548/410; 548/409; 546/16; 514/278

(58) Field of Classification Search ................. 514/409, 514/278; 548/410, 409; 546/16
See application file for complete search history.

(56) References Cited

U.S. PATENT DOCUMENTS

2008/0064643 A1*    3/2008    Carminati et al. .............. 514/16

FOREIGN PATENT DOCUMENTS

| EP | 0970957 A1 | 1/2000 |
| WO | WO 95/03303 | 2/1995 |

* cited by examiner

*Primary Examiner*—Charanjit S Aulakh
(74) *Attorney, Agent, or Firm*—Paul D. Strain; Fanelli, Strain & Haag, PLLC

(57) ABSTRACT

The present invention relates to novel 2-(6-oxo-1,7-diaza-spiro[4.4]non-7-yl)-propionamides of the formula

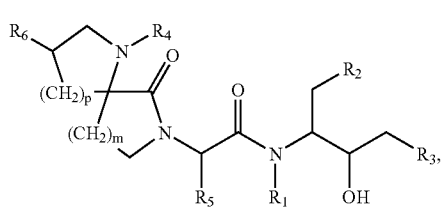

I wherein $R_1$, $R_2$, $R_3$, $R_4$, $R_5$, $R_6$, m and p are as defined in the specification, to their preparation, to their use as pharmaceuticals and to pharmaceutical compositions containing them.

4 Claims, No Drawings

CERTAIN SUBSTITUTED SPIROCYCLIC LACTAMS AND USE THEREOF AS PHARMACEUTICALS

This is a continuation of application Ser. No. 10/574,536 filed on Mar. 31, 2006, which is National Stage of International Application No. PCT/EP04/011054 filed on Apr. 10, 2004, the entire disclosures of which are hereby incorporated by reference.

The present invention relates to novel 2-(6-oxo-1,7-diaza-spiro[4.4]non-7-yl)-propionamides, to their preparation, to their use as pharmaceuticals and to pharmaceutical compositions containing them.

More particularly the invention relates to compounds of the formula

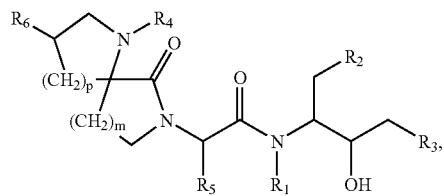

I wherein
$R_1$ is hydrogen or $(C_{1-4})$alkyl,
$R_2$ is optionally substituted $(C_{1-8})$alkyl, $(C_{3-7})$cycloalkyl, $(C_{3-7})$cycloalkyl$(C_{1-4})$alkyl, aryl or heteroaryl,
$R_3$ is —CH$(R_e)$C(=O)N$(R_a)R_b$ or —$(CH_2)_k$N$(R_c)R_d$, wherein
  k is 0, 1 or 2,
  $R_a$, $R_b$, $R_c$ and $R_d$, independently, are hydrogen or an optionally substituted $(C_{1-8})$alkyl, $(C_{5-9})$bicycloalkyl, $(C_{3-7})$cycloalkyl, $(C_{3-7})$cycloalkyl$(C_{1-4})$alkyl, aryl, aryl$(C_{1-4})$alkyl, heteroaryl, heteroaryl$(C_{1-4})$alkyl, 4-chromanyl, 1,2,3,4-tetrahydro-quinolin-4-yl, 1,2,3,4-tetrahydro-naphthalen-1-yl, thiochroman-4-yl-1,1-dioxide, 4 isochromanyl, 1,2,3,4-tetrahydro-isoquinolin-4-yl, thioisochroman-4-yl-1,1-dioxide, 1,1-dioxo-1,2,3,4-tetrahydro-1 lambda*6*-benzo[e][1,2]thiazin-4-yl, 1,1-dioxo-3,4-dihydro-1H-1lambda*6*-benzo[c][1,2]oxathiin-4-yl, 2,2-dioxo-1,2,3,4-tetrahydro-2lambda*6*-benzo[c][1,2]thiazin-4-yl or 2,2-dioxo-3,4-dihydro-2H-2lambda*6*-benzo[e][1,2]oxathiin-4-yl group, or
  $R_a$ and $R_b$ or $R_c$ and $R_d$, together with the nitrogen to which they are attached, form an optionally substituted pyrrolidinyl, piperidinyl, morpholinyl or piperazinyl group, and
  $R_e$ is $(C_{1-8})$alkyl, $(C_{1-4})$alkoxy$(C_{1-4})$alkyl, $(C_{3-7})$cycloalkyl or $(C_{3-7})$cycloalkyl$(C_{1-4})$alkyl,
$R_4$ is hydrogen or an optionally substituted $(C_{1-8})$alkyl, $(C_{1-4})$alkoxy$(C_{1-4})$alkyl, $(C_{3-7})$cycloalkyl, $(C_{3-7})$cycloalkyl$(C_{1-4})$alkyl, $(C_{2-6})$alkenyl, $(C_{2-6})$alkynyl, $(C_{3-7})$cycloalkoxy$(C_{1-4})$alkyl or aryl group,
$R_5$ is hydrogen or optionally substituted $(C_{1-4})$alkyl,
$R_6$ is hydrogen, hydroxy or halogen, and
m and p, independently, are 1 or 2, in free base form or in acid addition salt form.

On account of the asymmetrical carbon atoms present in the compounds of the formula I and their salts, the compounds may exist in optically active form or in the form of mixtures of optical isomers, e.g. in the form of racemic mixtures. All optical isomers and their mixtures, including the racemic mixtures, are part of the present invention.

Further, the compounds of the formula I and their salts may contain a radioisotope, such as tritium, $^{14}$C, $^{11}$C or $^{18}$F. All radiolabeled compounds and their use as biomarkers, in vitro or in vivo imaging agents, or in biochemical assays, e.g. binding assays, are part of the present invention.

Substituents on the above defined non-aromatic groups are selected from hydroxy, halogen, carbamoyl, carboxy, hydroxy$(C_{1-4})$alkyl, $(C_{1-4})$alkoxy, $(C_{1-4})$alkoxy$(C_{1-4})$alkyl, $(C_{1-4})$alkoxy$(C_{1-4})$alkoxy, $(C_{1-4})$alkylsulfanyl, $(C_{1-4})$alkoxycarbonyl, $(C_{1-4})$alkylcarbonyloxy, $(C_{1-4})$alkylcarbonyl, $(C_{1-4})$alkylsulfonyl, cyano, oxo, $(C_{3-7})$cycloalkyl, hetero$(C_{3-7})$cycloalkyl, optionally substituted aryl or optionally substituted heteroaryl. $(C_{3-7})$cycloalkyl or hetero-$(C_{3-7})$cycloalkyl groups can also be fused with an additional $(C_{3-7})$cycloalkyl, hetero$(C_{3-7})$cycloalkyl, or an aromatic or heteroaromatic ring.

Substituents on above defined aromatic or heteroaromatic groups are selected from halogen, hydroxy, cyano, nitro, trifluoromethyl, benzyloxy, phenoxy, $SO_2NH_2$, $NHSO_2(C_{1-3})$alkyl, carboxy, $(C_{1-4})$alkyloxycarbonyl, carbamoyl, $(C_{1-4})$alkylcarbamoyl, $(C_{1-4})$alkylsulfonyl, $(C_{1-4})$alkylcarbonyloxy, $(C_{1-4})$alkylcarbonyl, $(C_{1-6})$alkyl, $(C_{1-4})$alkoxy, hydroxy$(C_{1-4})$alkyl, aryl, heteroaryl or an optionally substituted amino group.

Substitutents on amino or carbamoyl groups can be one or two groups selected from $(C_{1-4})$alkyl, $(C_{1-4})$alkoxy$(C_{1-4})$alkyl, $(C_{1-4})$alkoxycarbonyl, aryl$(C_{1-4})$alkyloxycarbonyl or hetero-aryl$(C_{1-4})$alkyloxycarbonyl.

Aryl is an aromatic 6-membered ring optionally mono-, di- or tri-substituted by, independently, hydroxy, cyano, trifluoromethyl, halogen, carboxy, $(C_{1-4})$alkyloxycarbonyl, $(C_{1-4})$alkylcarbamoyl, $(C_{1-4})$alkylsulfonyl, $(C_{1-4})$alkylcarbonyloxy, $(C_{1-4})$alkylcarbonylamino, $(C_{1-4})$alkylcarbonyl, $(C_{1-6})$alkyl, $(C_{1-4})$alkoxy or hydroxy$(C_{1-4})$alkyl. Aryl groups can also be fused with a $(C_{3-7})$cycloalkyl, hetero$(C_{3-7})$cycloalkyl or additional aromatic or heteroaromatic ring (e.g. to form a naphthyl, quinolinyl or indolyl group).

Heteroaryl is an aromatic 5- or 6-membered ring, in which 1, 2 or 3 atoms are heteroatoms independently selected from O, N and S. Heteroaryl is, for example, 1-methyl-1H-pyrrol-2-yl or 1H-imidazol-2-yl. It can also be fused with a cycloalkyl or additional aromatic or heteroaromatic ring (e.g. to form a quinolinyl or indolyl group).

Halogen denotes fluorine, bromine, chlorine or iodine.

Any alkyl, alkenyl, alkynyl or alkoxy group is straight or branched.

Unless defined otherwise, carbon containing groups and molecules contain 1 to 8, preferably 1 to 6, more preferably 1 to 4, carbon atoms.

In a preferred embodiment, the invention relates to a compound of the formula I, in free base form or in acid addition salt form, in which $R_1$ is hydrogen.

In another preferred embodiment, the invention relates to a compound of the formula I, in free base form or in acid addition salt form, in which $R_2$ is aryl, preferably phenyl, more preferably unsubstituted phenyl.

In another preferred embodiment, the invention relates to a compound of the formula I, in free base form or in acid addition salt form, in which $R_3$ is —CH$(R_e)$C(=O)N$(R_a)R_b$ or —$(CH_2)_k$N$(R_c)R_d$, wherein k is 0; $R_a$ is hydrogen; $R_b$ is $(C_{1-8})$alkyl or $(C_{5-9})$bicycloalkyl such as bicycloheptyl; $R_c$ is hydrogen; $R_d$ is optionally substituted aryl$(C_{1-4})$alkyl, preferably benzyl substituted in the phenyl ring by $(C_{1-4})$alkyl, or is optionally substituted $(C_{3-7})$cycloalkyl, preferably cyclopropyl substituted by phenyl optionally substituted by halogen, such as bromine, or is 4-chromanyl optionally substituted, preferably by halogen and/or $(C_{1-4})$alkyl; and $R_e$ is $(C_{1-4})$alkyl.

In another preferred embodiment, the invention relates to a compound of the formula I, in free base form or in acid addition salt form, in which $R_4$ is $(C_{1-8})$alkyl, or is $(C_{1-8})$alkyl substituted, preferably mono-substituted, by $(C_{3-7})$cycloalkyl, preferably cyclopropyl, by halogen, such as fluorine, by $(C_{1-4})$alkoxy, or by hydroxy, or is $(C_{2-6})$alkenyl optionally substituted, preferably mono-substituted, by hydroxy, or is $(C_{2-6})$alkynyl, or is aryl, preferably phenyl, preferably unsubstituted phenyl.

In another preferred embodiment, the invention relates to a compound of the formula I, in free base form or in acid addition salt form, in which $R_4$ is 2,2,3,3-tetratritiopropyl.

In another preferred embodiment, the invention relates to a compound of the formula I, in free base form or in acid addition salt form, in which $R_5$ is $(C_{1-8})$alkyl, preferably $(C_{1-4})$alkyl.

In another preferred embodiment, the invention relates to a compound of the formula I, in free base form or in acid addition salt form, in which $R_6$ is hydrogen or halogen, preferably hydrogen or fluorine.

In another preferred embodiment, the invention relates to a compound of the formula I, in free base form or in acid addition salt form, in which m is 1.

In another preferred embodiment, the invention relates to a compound of the formula I, in free base form or in acid addition salt form, in which p is 1.

In a further aspect, the invention relates to a process for the preparation of the compounds of the formula I and their salts, comprising the steps of acylating a compound of the formula

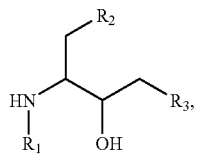

II wherein $R_1$, $R_2$ and $R_3$ are as defined above for the formula I, with an acid of the formula

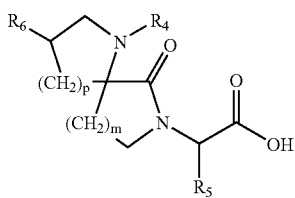

III wherein $R_4$, $R_5$, $R_6$, m and p are as defined above for the formula I, or an activated form, such as an ester or an acid halogenide, thereof and recovering the so obtainable compound of the formula I in free base form or in acid addition salt form.

The reaction can be effected according to conventional methods, for example as described in the examples.

The compounds of the formula I can also be produced by further conventional processes, e.g. as described in the examples.

The starting materials of the formulae II and III are known or may be prepared according to conventional procedures starting from known compounds, for example as described in the examples.

The working-up of the reaction mixtures and the purification of the compounds thus obtainable may be carried out in accordance with known procedures.

Acid addition salts may be produced from the free bases in known manner, and vice-versa.

Compounds of the formula I and their pharmaceutically acceptable acid addition salts, hereinafter referred to as agents of the invention; exhibit valuable pharmacological properties when tested in vitro and in animals, and are therefore useful as pharmaceuticals.

The agents of the invention are inhibitors of aspartic proteases and can be used for the treatment of disorders involving processing by such enzymes. Particularly they inhibit beta-secretase and as such inhibit the generation of beta-amyloid and the subsequent aggregation into oligomers and fibrils.

In addition, the agents of the invention exhibit valuable properties as histopathological labeling agents, imaging agents and/or biomarkers, hereinafter "markers", for the selective labeling of BACE (beta-secretase cleaving enzyme).

More particularly the agents of the invention are useful as markers for labeling BACE in vitro or in vivo (see Examples 9 and 10).

The agents of the invention are therefore useful, for instance, for determining the levels of active site occupancy of a drug acting at BACE, or for diagnostic purposes for diseases resulting from a dysfunction of BACE-related processes, and for monitoring the effectiveness of pharmacotherapies of such diseases.

In accordance with the above, the present invention also provides an agent of the invention for use as a marker for neuroimaging.

In a further aspect, the present invention provides a composition for labeling brain and peripheral structures involving BACE in vivo and in vitro comprising an agent of the invention.

In still a further aspect, the present invention provides a method for labeling brain and peripheral structures involving BACE in vitro or in vivo, which comprises contacting brain or peripheral tissue with an agent of the invention.

The method of the invention may comprise a further step aimed at determining whether the agent of the invention labeled the target structure. Said further step may be effected by observing the target structure using autoradiography, positron emission tomography (PET), or any device allowing detection of radioactive radiations.

Test 1: Inhibition of Human BACE

Recombinant BACE (extracellular domain, expressed in baculovirus and purified using standard methods) at 6 nM concentration is incubated with the test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) is added to a final concentration of 3 μM and the increase in fluorescence is recorded at excitation of 325 nm and emission at 400 nm in a microplate spectro-fluorimeter for 20 minutes in 1-minute intervals. $IC_{50}$ values are calculated from percentage of inhibition of BACE-activity as a function of the test compound concentration.

Test 2: Inhibition of Human BACE-2

Recombinant BACE-2 (extracellular domain, expressed in baculovirus and purified using standard methods) at 2.5 nM concentrations is incubated with the test compound at various concentrations for 1 hour at room temperature in 100 mM acetate buffer, pH 4.5, containing 0.1% CHAPS. Synthetic peptide substrate Mca-Ser-Glu-Val-Asn-Leu-Asp-Ala-Glu-Phe-Lys(DNP) is added to a final concentration of 3 µM and the increase in fluorescence is recorded at excitation of 325 nm and emission at 400 nm in a microplate spectrofluorimeter for 20 minutes in 1-minute intervals. $IC_{50}$ values are calculated from percentage of inhibition of BACE-2-activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in 100 mM sodium formate buffer, pH 3.1. Synthetic peptide substrate Mca-Gly-Lys-Pro-Ile-Leu-Phe-Phe-Arg-Leu-Lys(DNP)-D-Arg-$NH_2$ is added to a final concentration of 2 µM and the increase in fluorescence is recorded at excitation of 325 nm and emission at 400 nm in a microplate spectrofluorimeter for 20 minutes in 1-minute intervals. $IC_{50}$ values are calculated from percentage of inhibition of cathepsin D-activity as a function of the test compound concentration.

Test 4: Inhibition of Cellular Release of Amyloid Peptide 1-40

Chinese hamster ovary cells are transfected with the gene for amyloid precursor protein. Cells are plated at a density of 8000 cells/well in a 96-well microtiter plate and cultivated for 24 hours in DMEM cell culture medium containing 10% FCS. The test compound is added to the cells at various concentrations, and cells are cultivated for 24 hours in the presence of the test compound. The supernatants are collected, and the concentration of amyloid peptide 1-40 is determined using sandwich ELISA. The potency of the compound is calculated from the percentage of inhibition of amyloid peptide release as a function of the test compound concentration.

In at least one of the above-indicated tests, the agents of the invention show activity at concentrations below 20 µM.

The agents of the invention are therefore useful e.g. for the treatment and/or prevention of neurological and vascular disorders related to beta-amyloid generation and/or aggregation, such as neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis.

Some of the agents of the invention also inhibit BACE2 (beta-site APP cleaving enzyme 2) or Cathepsin D, close homologues of the pepsin-type aspartyl proteases. Due to the correlation of BACE2 and CathD expression with a more tumorigenic and metastatic potential of tumor cells, such inhibitors are useful for the suppression of the metastasis process associated with tumor cells.

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range from about 10 to about 2000, preferably from about 10 to about 200, mg of an agent of the invention conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of neurological or vascular disorders related to beta-amyloid generation and/or aggregation.

The present invention furthermore provides a pharmaceutical composition comprising an agent of the invention in association with at least one pharmaceutical carrier or diluent. Such compositions may be manufactured in conventional manner. Unit dosage forms contain, for example, from about 1 to about 1000, preferably from about 1 to about 500, mg of an agent of the invention.

The agents of the invention can be administered alone or in combination with other pharmaceutical agents effective in the treatment of conditions mentioned above.

The pharmaceutical combination may be in the form of a unit dosage form, whereby each unit dosage will comprise a predetermined amount of the two components, in admixture with suitable pharmaceutical carriers or diluents. Alternatively, the combination may be in form of a package containing the two components separately, e.g. a pack or dispenser-device adapted for the concomitant or separate administration of the two active agents, wherein these agents are separately arranged.

Moreover the present invention provides the use of an agent of the invention, for the manufacture of a medicament for the treatment of any neurological or vascular disorders related to beta-amyloid generation and/or aggregation.

In still a further aspect, the present invention provides a method for the treatment of any neurological or vascular disorders related to beta-amyloid generation and/or aggregation, in a subject in need of such treatment, which comprises administering to such subject a therapeutically effective amount of an agent of the invention.

The following Examples illustrate the invention.

Abbreviations

BOC tert-butoxycarbonyl
BOP benzotriazol-1-yloxytris(dimethylamino)phosphonium hexafluorophosphate
DAST (Diethylamino)sulfur trifluoride
DCM dichloromethane
DMF N,N-dimethylformamide
DMPU N,N'-dimethylpropyleneurea
EDC.HCl 1-ethyl-3-[3-(dimethylamino)propyl]-carbodiimide hydrochloride
EtOAc ethylacetate
h hours
HCl hydrochloric acid
HOBt hydroxybenzotriazole
HPLC high pressure liquid chromatography
LAH lithium aluminum hydride
min minutes
Mp melting point
MS mass spectroscopy
Rf retention factor (TLC)
rt room temperature
TBAF tetrabutylammonium fluoride TBME tert-butyl methyl ether
TBTU O-(benzotriazol-1-yl)-N,N,N',N'-tetramethyluronium-tetrafluoroborate
TFA trifluoroacetic acid
THF tetrahydrofuran
TLC thin-layer chromatography

EXAMPLE 1

4-(S)-hydroxy-5-(S)-[2-(S)-(1-isobutyl-6-oxo-1,7-diaza-spiro(S)-[4.4]non-7-yl)-propionylamino]-2-(R)-methyl-6-phenyl-hexanoic acid butylamide 113 mg (0.4 mmol) of 2-(S)-(1-isobutyl-6-oxo-1,7-diaza-spiro-(S)[4.4]non-7-yl)propionic acid methyl ester are dissolved in 18 ml of THF and treated with 2 mL of a 0.5 N aqueous LiOH solution and stirred at room temperature for four hours. The reaction mixture is cooled to 5° C. and treated with an aqueous 1 N HCl solution until a pH of 4 is reached. The solution is submitted to two consecutive azeotropic evaporations with 80 mL toluene and the residue dried under high vacuum, then taken up in 20 mL dichloromethane and stirred at room temperature for twenty hours with 117 mg (0.4 mmol) 5-(S)-amino-4-(S)-hydroxy-2-(R)-methyl-6-phenyl-hexanoic acid butylamide, 85 mg (0.44 mmol) EDC.HCl, 54 mg (0.4 mmol) HOBt and 0.17 mL triethylamine (1.2 mmol). The reaction mixture is quenched with 10 mL ice-cold saturated aqueous sodium bicarbonate solution, then extracted twice with dichloromethane. The combined organic phases are evaporated and the residue is column chromatographed (silica gel, TBME/EtOAc/EtOH 49:59:2) to yield after evaporation of the pure fractions the desired product as a colorless resin.

MS (EI+): 453 (M+1)

The starting materials can be prepared as described hereafter:

a) 2-(S)-(1-isobutyl-6-oxo-1,7-diaza-spiro-(S)-[4.4]non-7-yl)-propionic acid methyl ester 260 mg (0.8 mmol) 7-(1-methoxycarbonyl-(S)-ethyl)-6-oxo-1,7-diaza-spiro-(S)-[4.4]nonane-1-carboxylic acid tert-butyl ester is stirred in 3 mL of a 4N solution HCl in dioxane for three hours at room temperature, then evaporated. The residue is taken up in toluene and evaporated to dryness (twice), then taken up in 6 mL methanol, treated with 0.145 mL (1.6 mmol) isobutylaldehyde, 300 mg 3 Å powdered molecular sieve and 100 mg (1.6 mmol) sodium cyanoborohydride and stirred overnight at room temperature. The reaction mixture is treated with 4 mL saturated aqueous ammonium chloride solution and after 10 minutes with 8 mL saturated aqueous sodium bicarbonate, then extracted with EtOAc. The combined organic phases are evaporated and the residue column chromatographed (silica gel, EtOAc) W to yield after evaporation of the corresponding fractions the desired product as a colorless oil.

MS (ES+): 283 (M+1)

b) 7-(1-methoxycarbonyl-(S)-ethyl)-6-oxo-1,7-diaza-spiro-(R)-[4.4]nonane-1-carboxylic acid tert-butyl ester and 7-(1-Methoxycarbonyl-(S)-ethyl)-6-oxo-1,7-diaza-spiro-(S)-[4.4]nonane-1-carboxylic acid tert-butyl ester 4.3 g (12 mmol) 2-[2-(1-methoxycarbonyl-ethylamino)-(S)-ethyl]-pyrrolidine-1,2-dicarboxylic acid 1-tert-butyl ester 2-methyl ester are dissolved in 60 mL xylene and heated to 150° C. for two hours. The reaction mixture is evaporated and the residue column chromatographed (silica gel, EtOAc/petroleum ether 3:2) to yield 1.85 g (46%) 7-(1-methoxycarbonyl-S)-ethyl)-6-oxo-1,7-diaza-spiro-(R)-[4.4]nonane-1-carboxylic acid tert-butyl ester and 1.8 g (45%) 7-(1-methoxycarbonyl-(S)-ethyl)-6-oxo-1,7-diaza-spiro-(S)-[4.4]nonane-1-carboxylic acid tert-butyl ester. The absolute stereochemistry is confirmed by X-ray of a sample recrystallized in diisopropylether.

c) 2-[2-(1-methoxycarbonyl-(S)-ethylamino)-ethyl]-pyrrolidine-1,2-dicarboxylic acid 1-tert-butyl ester 2-methyl ester 271 mg (1 mmol) 2-(2-oxo-ethyl)-pyrrolidine-1,2-dicarboxylic acid 1-tert-butyl ester 2-methyl ester and 154 mg (1.1 mmol) L-alanine methyl ester hydrochloride are suspended in 10 mL toluene and treated with 0.073 mL (1 eq.) triethylamine. The reaction mixture is stirred 10 minutes at room temperature and slowly evaporated in a rotary evaporator. The residue is taken up in 15 mL acetonitrile and 95 mg (1.5 mmol) sodium cyanoborohydride in 2 mL methanol added dropwise. Upon completion of the reaction (TLC, EtOAc/petroleum ether 4:1), the reaction mixture is evaporated and the residue taken up in ethyl acetate and treated with an ice-cold, saturated aqueous ammonium chloride solution, then extracted with ethyl acetate and saturated aqueous sodium bicarbonate. The combined organic phases are dried over sodium sulfate, filtered and evaporated to yield the crude desired product as a thick oil.

MS (EI+): 359 (M+1)

Rf (EtOAc): 0.22 d) 5-(S)-amino-4-(S)-hydroxy-2-(R)-methyl-6-phenyl-hexanoic acid butylamide 32 mg (0.1 mmol) [1-(4-(R)-methyl-5-oxo-tetrahydro-furan-2-(S)-yl)-2-(S)-phenyl-ethyl]-carbamic acid tert-butyl ester are stirred at room temperature for two hours in 1 mL of a 4N HCl solution in dioxane. The reaction mixture is evaporated to dryness, the residue taken up in toluene and evaporated to dryness twice before drying under high vacuum. The residue is taken up in 1 mL (excess) butylamine and stirred at 25° C. overnight then evaporated and the residue extracted twice with ethyl acetate and saturated sodium bicarbonate. The combined organic phases are evaporated, the crude desired product obtained quantitatively as a colorless resin and used without further purification.

(MS (EI+): 293 (M+1).

The following compounds can be obtained by a similar procedure:

EXAMPLE 1A 5-(S)-[2-(S)-(1-cyclopropylmethyl-6-oxo-1,7-diaza-spiro-(S)-[4.4]non-7-yl)-propionylamino]-4-(S)-hydroxy-2-(R)-methyl-6-phenyl-hexanoic acid butylamide

MS (EI+): 541 (M+1)

EXAMPLE 1B 5-(S)-[2-(S)-(1-propyl-6-oxo-1,7-diaza-spiro-(S)-[4.4]non-7-yl)-propionylamino]-4-(S)-hydroxy-2-(R)-methyl-6-phenyl-hexanoic acid butylamide

MS (EI+): 529 (M+1)

EXAMPLE 1C 5-(S)-[2-(S)-(1-phenyl-6-oxo-1,7-diaza-spiro-(S)[4.4]non-7-yl)-propionylamino]-4-(S)-hydroxy-2-(R)-methyl-6-phenyl-hexanoic acid butylamide

MS (EI+): 591 (M+1)

EXAMPLE 1D 5-(S)-[2-(S)-(1-phenyl-6-oxo-1,7-diaza-spiro-(R)-[4.4]non-7-yl)-propionylamino]-4-(S)-hydroxy-2-(R)-methyl-6-phenyl-hexanoic acid butylamide

MS (EI+): 591 (M+1)

EXAMPLE 1E 4-(S)-hydroxy-2-(R)-methyl-5-(S)-[2-(S)-(6-oxo-1-propyl-1,7-diaza-spiro-(S)-[4.4]non-7-yl)-propionylamino]-6-phenyl-hexanoic acid (2,2-dimethyl-propyl)-amide

MS (EI+): 543 (M+1)

EXAMPLE 1F 5-(S)-[2-(S)-(1-cyclopropylmethyl-6-oxo-1,7-diaza-spiro-(S)-[4.4]non-7-yl)-propionylamino]-4-(S)-hydroxy-2-(R)-methyl-6-phenyl-hexanoic acid bicyclo[2.2.1]hept-exo-2-(R,S)-ylamide

MS (EI+): 579 (M+1)

EXAMPLE 1G 5-(S)-{2-(S)-[1-(2,2-dimethyl-propyl)-6-oxo-1,7-diaza-spiro-(S)-[4.4]non-7-yl]-propionylamino}-4-(S)-hydroxy-2-(R)-methyl-6-phenyl-hexanoic acid butylamide

MS (EI+): 557 (M+1)

EXAMPLE 1H 4-(S)-hydroxy-5-(S)-{2-(S)-[1-(3-methoxy-propyl)-6-oxo-1,7-diaza-spiro-(S)-[4.4]non-7-yl]-propionylamino}-2-(R)-methyl-6-phenyl-hexanoic acid butylamide

MS (EI+): 559 (M+1)

EXAMPLE 1I 5-(S)-[2-(S)-(1-cyclopropylmethyl-6-oxo-1,7-diaza-spiro-(R)-[4.4]non-7-yl)-propionylamino]-4-(S)-hydroxy-2-(R)-methyl-6-phenyl-hexanoic acid bicyclo[2.2.1]hept-exo-2-(R,S)-ylamide

MS (EI+): 579 (M+1)

EXAMPLE 1J 4-(S)-hydroxy-5-(S)-{2-(S)-[1-(3-methoxy-propyl)-6-oxo-1,7-diaza-spiro(R)-[4.4]non-7-yl]-propionylamino}-2-(R)-methyl-6-phenyl-hexanoic acid butylamide

MS (EI+): 559 (M+1)

EXAMPLE 1K 5-(S)-[2-(S)-(1-propyl-6-oxo-1,7-diaza-spiro(R)-[4.4]non-7-yl)-propionylamino]-4-(S)-hydroxy-2-(R)-methyl-6-phenyl-hexanoic acid butylamide

MS (EI+): 529 (M+1)

EXAMPLE 1L 4-(S)-hydroxy-5-(S)-[2-(S)-(1-(2-fluoroethyl)-6-oxo-1,7-diaza-spiro(S)-[4.4]non-7-yl)-propionylamino]-2-(R)-methyl-6-phenyl-hexanoic acid butylamide

MS (EI+): 533 (M+1)

EXAMPLE 2

5-(S)-[2-(S)-(1-allyl-6-oxo-1,7-diaza-spiro-(R)-[4.4]non-7-yl)-propionylamino]-4-(S)-hydroxy-2-(R)-methyl-6-phenyl-hexanoic acid butylamide 52 mg (0.1 mmol) 4-(S)-hydroxy-2-(R)-methyl-5-(S)-[2-(S)-(6-oxo-1,7-diaza-spiro-(R)-[4.4]non-7-yl)-propionylamino]-6-phenyl-hexanoic acid butyl amide hydrochloride, 28 mg potassium carbonate and 0.01 mL allyl bromide are stirred at room temperature for 65 hours in 3 mL DMF, then extracted with EtOAc and brine (twice). The combined organic phases are dried over sodium sulfate, evaporated and column chromatographed to yield the desired product as a light-colored resin.

MS (EI+): 527 (M+1)

The starting materials can be prepared as described hereafter:

a) 4-(S)-hydroxy-2-(R)-methyl-5-(S)-[2-(S)-(6-oxo-1,7-diaza-spiro-(R)-[4.4]non-7-yl)-propionylamino]-6-phenyl-hexanoic acid butyl amide hydrochloride 170 mg (0.33 mmol) 7-{1-(S)-[1-(S)-(4-(R)-methyl-5-oxo-tetrahydro-furan-2-(S)-yl-2-phenyl-ethylcarbamoyl]-ethyl}-6-oxo-1,7-diaza-spiro-(R)-[4.4]nonane-1-carboxylic acid tert-butyl ester are dissolved in 1.5 mL (excess) butylamine and heated to 65° C. under argon for two hours. The reaction mixture is evaporated, the residue taken up in toluene and evaporated to dryness, redissolved in 5 mL isopropanol, treated with 1 mL of a 6N HCl solution in isopropanol and stirred at room temperature for four hours, then evaporated, taken up in toluene and evaporated again to yield the desired product, which is used without further purification.

MS (EI+): 487 (M+1)

b) 7-{1-(S)-[1-(S)-(4-(R)-methyl-5-oxo-tetrahydro-furan-2-(S)-yl)-2-phenyl-ethylcarbamoyl]-ethyl}-6-oxo-1,7-diaza-spiro-(R)-[4.4]nonane-1-carboxylic acid tert-butyl ester and 7-{1-(S)-[1-(R)-(4-(S)-methyl-5-oxo-tetrahydro-furan-2-(R)-yl)-2-phenyl-ethylcarbamoyl]-ethyl}-6-oxo-1,7-diaza-spiro-(R)-[4.4]nonane-1-carboxylic acid tert-butyl ester 326 mg (1 mmol) 7-(1-(S)-methoxycarbonyl-ethyl)-6-oxo-1,7-diaza-spiro-(R)-[4.4]nonane-1-carboxylic acid tert-butyl ester are dissolved in 15 mL THF, cooled to 10° C. and treated with 7 mL (1.05 eq) of a 0.15 N THF solution of LiOH. After two hours stirring at room temperature, a 1 N aqueous HCl solution is added until a pH of 4 was reached, and the reaction mixture evaporated. The residue is taken up in toluene, evaporated to dryness and dried under high vacuum, then taken up in 20 mL dichloromethane and stirred for 18 hours after addition of 230 mg racemic 5-(1-amino-2-phenyl-ethyl)-3-methyl-dihydro-furan-2-one, 135 mg HOBt (1 mmol), 208 mg EDC.HCl (1.1 mmol) and 0.031 mL triethylamine (2.25 mmol). The reaction mixture is extracted with EtOAc and saturated aqueous sodium bicarbonate, the combined organic fractions are washed with brine, evaporated and column chromatographed (silica gel, EtOAc/diisopropylether 4:1) to yield 7-{1-(S)-[1-(S)-(4-(R)-methyl-5-oxo-tetrahydro-furan-2-(S)-yl)-2-phenyl-ethylcarbamoyl]-ethyl}-6-oxo-1,7-diaza-spiro-(R)-[4.4]nonane-1-carboxylic acid tert-butyl ester and 7-{1-(S)-[1-(R)-(4-(S)-methyl-5-oxo-tetrahydro-furan-2-(R)-yl)-2-phenyl-ethylcarbamoyl]-ethyl}-6-oxo-1,7-diaza-spiro-(R)-[4.4]nonane-1-carboxylic acid tert-butyl ester is white solids in respectively 33 and 30% yields.

The absolute stereochemistry is confirmed by comparison with optically pure material made from 5-(S)-(1-(S)-amino-2-phenyl-ethyl)-3-(R)-methyl-dihydro-furan-2-one.

MS (EI+): 514 (M+1)

The following compounds can be obtained by a similar procedure:

EXAMPLE 2A 5-(R)-[2-(S)-(1-allyl-6-oxo-1,7-diaza-spiro-(R)-[4.4]non-7-yl)-propionylamino]-4-(R)-hydroxy-2-(S)-methyl-6-phenyl-hexanoic acid butylamide

MS (EI+): 527 (M+1)

EXAMPLE 2B 5-(R)-[2-(S)-(1-allyl-6-oxo-1,7-diaza-spiro(S)-[4.4]non-7-yl)-propionylamino]-4-(R)-hydroxy-2-(S)-methyl-6-phenyl-hexanoic acid butylamide

MS (EI+): 527 (M+1)

EXAMPLE 2C 5-(S)-[2-(S)-(1-allyl-6-oxo-1,7-diaza-spiro-(S)-[4.4]non-7-yl)-propionylamino]-4-(S)-hydroxy-2-(R)-methyl-6-phenyl-hexanoic acid butylamide

MS (EI+): 527 (M+1)

EXAMPLE 3

4-(S)-hydroxy-5-(S)-{2-(S)-[1-(4-hydroxy-butyl)-6-oxo-1,7-diaza-spiro-(R)-[4.4]non-7-yl]-propionylamino}-2-(R)-methyl-6-phenyl-hexanoic acid butylamide 30 mg (0.06 mmol) 4-(7-{1-(S)-[1-(S)-(4-(R)-methyl-5-oxo-tetrahydro-furan-2-(S)-yl)-2-phenyl-ethylcarbamoyl]-ethyl}-6-oxo-1,7-diaza-spiro-(R)-[4.4]non-1-yl)-butyric acid methyl ester are stirred overnight at room temperature in 1 mL butylamine. The reaction mixture is evaporated to dryness, taken up in toluene and evaporated again, and the residue dissolved in THF, cooled to 5° C. and treated with 3 mg (2 eq.) lithium borohydride. After stirring for two hours at room temperature, the reaction mixture is cooled below 10° C., quenched with 2 mL of saturated aqueous ammonium chloride and 2 mL of saturated aqueous sodium bicarbonate and stirred an additional 10 minutes before extraction with EtOAc (twice). The combined organic phases are dried over sodium sulfate, evaporated, and the residue column chromatographed (silica gel, DCM/EtOH/ammonia 90:10:0.05) to yield the desired product as a light-colored resin.

MS (EI+): 559 (M+1)

The starting materials can be prepared as described hereafter:

a) 4-(7-{1-(S)-[1-(S)-(4-(R)-methyl-5-oxo-tetrahydro-furan-2-(S)-yl)-2-phenyl-ethylcarbamoyl]-ethyl}-6-oxo-1,7-diaza-spiro-(R)-[4.4]non-1-yl)-butyric acid methyl ester 30 mg (0.06 mmol) 4-(7-{1-(S)-[1-(S)-(4-(R)-methyl-5-oxo-tetrahydro-furan-2-(S)-yl)-2-phenyl-ethylcarbamoyl]-ethyl}6-oxo-1,7-diaza-spiro-(R)-[4.4]non-1-yl)-but-2-enoic acid methyl ester are stirred in THF under hydrogen for two hours in the presence of a catalytic amount of 10% Pd/C, then filtered through celite and evaporated to yield 30 mg desired product, which is used without further purification.

MS (EI+): 514 (M+1)

b) 4-(7-{1-(S)-[1-(S)-(4-(R)-methyl-5-oxo-tetrahydro-furan-2-(S)-yl)-2-phenyl-ethylcarbamoyl]-ethyl}-6-oxo-1,7-diaza-spiro-(R)-[4.4]non-1-yl)-but-2-enoic acid methyl ester 130 mg (0.25 mmol) 7-{1-(S)-[1-(S)-(4-(R)-methyl-5-oxo-tetrahydro-furan-2-(S)-yl)-2-phenyl-ethylcarbamoyl]-ethyl}-6-oxo-1,7-diaza-spiro-(R)[4.4]nonane-1-carboxylic acid tert-butyl ester are dissolved in 2 mL of 4N HCl in dioxane. The reaction mixture is evaporated after 90 minutes, taken up in toluene and evaporated to dryness. The residue is taken up in dichloromethane and stirred at room temperature for 18 hours in the presence of 92 mg (1 eq.) tetrabutylammonium iodide, 0.03 mL trans-4-bromobut-2-enoic acid methyl ester and 0.09 mL (2 eq.) diisopropylethylamine. The reaction mixture is extracted with dichloromethane and aqueous bicarbonate (twice), the combined organic phases evaporated and the residue column chromatographed (silica gel, EtOAc) to yield the desired product as a slightly brownish resin.

MS (EI+): 512 (M+1)

The following compound can be obtained by a similar procedure:

EXAMPLE 3A 4-(S)-hydroxy-5-(S)-{2-(S)-[1-(4-hydroxy-butyl)-6-oxo-1,7-diaza-spiro-(S)-[4.4]non-7-yl]-propionylamino}-2-(R)-methyl-6-phenyl-hexanoic acid butylamide

MS (EI+): 559 (M+1)

EXAMPLE 4

4-hydroxy-5-{2-[1-(4-hydroxy-but-2-enyl)-6-oxo-1,7-diaza-spiro[4.4]non-7-yl]-propionylamino}-2-methyl-6-phenyl-hexanoic acid butylamide

MS (EI+): 557 (M+1)

is obtained in a similar manner to example 1, but using 2-[1-(4-hydroxy-but-2-enyl)-6-oxo-1,7-diaza-spiro[4.4]non-7-yl]-propionic acid methyl ester in step 1a.

The starting material can be prepared as described hereafter:

2-[1-(4-hydroxy-but-2-enyl)-6-oxo-1,7-diaza-spiro[4.4]non-7-yl]-propionic acid methyl ester 82 mg (0.25 mmol) (S,S)-7-(1-methoxycarbonyl-ethyl)-6-oxo-1,7-diaza-spiro[4.4]nonane-1-carboxylic acid tert-butyl ester are stirred at room temperature for three hours in 1 mL of a 4N HCl dioxane solution, evaporated, then taken up in toluene and evaporated again (twice). The residue is taken up in 2 mL dichloromethane and stirred at room temperature for 65 hours in the presence of 74 mg (0.2 mmol) tetrabutylammonium iodide, 0.035 mL (0.2 mmol) diisopropylethylamine and 30 mg (0.2 mmol) 4-bromo-but-2-en-1-ol. The reaction mixture is extracted with EtOAc and saturated aqueous sodium bicarbonate, the combined organic phases washed with brine, evaporated to dryness and the residue column chromatographed (silica gel, EtOAc/EtOH 9:1) to yield the desired product as a thick liquid.

MS (EI+): 297 (M+1)

EXAMPLE 5

5-(S)-[2-(S)-(3-(S)-fluoro-6-oxo-1-propyl-1,7-diaza-spiro-(S)-[4.4]non-7-yl)-propionylamino]-4-(S)-hydroxy-2-(R)-methyl-6-phenyl-hexanoic acid butylamide This compound can be synthesized as described in Example 1, starting from (1R,4S)-4-fluoro-2-(2-oxo-ethyl)-pyrrolidine-1,2-dicarboxylic acid 1-tert-butyl ester 2-methyl ester instead of 2-(2-oxo-ethyl)-pyrrolidine-1,2-dicarboxylic acid 1-tert-butyl ester 2-methyl ester.

MS (EI+): 547 (M+1)

The starting materials can be made as follows:

a) (2R,4S)-4-fluoro-2-(2-oxo-ethyl)-pyrrolidine-1,2-dicarboxylic acid 1-tert-butyl ester 2-methyl ester 1 g (3.5 mmol) (2R,4S)-2-allyl-4-fluoro-pyrrolidine-1,2-dicarboxylic acid 1-tert-butyl ester 2-methyl ester is dissolved in 60 mL dichloromethane/methanol 1:1, cooled to −78° C., flushed with oxygen for two minutes then treated with a flux of ozone until the solution turns light blue. The solution is allowed to warm up to room temperature after addition of 1 g (1.1 eq.) triphenylphosphine, stirred an additional 5 h and column chromatographed (silica gel, TBME/petroleum ether 3:2) to yield 870 mg of the desired product as a clear oil.

MS (EI+): 290 (M+1).

b) (2R,4S)-2-allyl-4-fluoro-pyrrolidine-1,2-dicarboxylic acid 1-tert-butyl ester 2-methyl ester 0.39 mL DAST (1.2 eq) are dissolved in 30 mL dichloromethane, cooled to −78° C. and treated over 10 min. with a dropwise addition of 10 mL dichloromethane containing 1.8 g (6.3 mmol) (2R,4R)-2-allyl-4-hydroxy-pyrrolidine-1,2-dicarboxylic acid 1-tert-butyl ester 2-methyl ester. The solution is allowed to reach room temperature under stirring, over 2 h. After cooling below 5° C. the reaction mixture is treated with an ice-old saturated aqueous sodium carbonate solution and extracted with dichloromethane. The combined extracts are washed with brine and dried over sodium sulphate, evaporated and the residue column chromatographed (silica gel, TBME/petroleum ether 1:1) to yield 1 g desired product as a colorless thick oil.

MS (EI+): 288 (M+1)

c) (2R,4R)-2-allyl-4-hydroxy-pyrrolidine-1,2-dicarboxylic acid 1-tert-butyl ester 2-methyl ester 3.3 g (8.27 mmol) (2R,4R)-(2-allyl-4-(tert-butyl-dimethyl-silanyloxy)-pyrrolidine-1,2-dicarboxylic acid 1-tert-butyl ester 2-methyl ester are dissolved in 60 mL THF, cooled below 5° C. and treated with 8.68 mL (1.05 eq) 1 M TBAF in THF under stirring. The reaction mixture is allowed to slowly reach room temperature, while being stirred another 4 h. Ice and AcOEt are added, the mixture washed with brine twice, and the organic phase evaporated to yield a crude product which is column chromatographed (silica gel, TBME/petroleum ether 1:1) to yield 1.8 g desired product as a colorless, thick oil, which is used as such in the next step.

EXAMPLE 6

(S)—N-[(1S,2R)-1-benzyl-2-hydroxy-3-(3-isopropyl-benzylamino)-propyl]-2-((S)-6-oxo-1-propyl-1,7-diaza-spiro[4.4]non-7-yl)-propionamide A solution of 100 mg (2R,3S)-3-amino-1-(3-isopropyl-benzylamino)-4-phenyl-butan-2-ol dihydrochloride, 79 mg (S)-2-((S)-6-oxo-1-propyl-1,7-diaza-spiro[4.4]non-7-yl)-propionic acid, 102 mg TBTU and 0.171 mL N-methyl morpholine in 5 mL $CH_2Cl_2$ is stirred for 5 h at ambient temperature. The solution is diluted with DCM and subsequently washed with bicarbonate, brine, 0.1N HCl and bicarbonate. After drying with $MgSO_4$ all volatiles are evaporated in vacuo and the product is purified by column chromatography (silica gel, DCM/MeOH 95:5) to give 53 mg (37%) of the desired product.

MS-ESI+: 549 [M+]

Rf: 0.28 ($CH_2Cl_2$/MeOH=9/1)

The starting material can be prepared as described hereafter:

a) (2R,3S)-3-amino-1-(3-isopropyl-benzylamino)-4-phenyl-butan-2-ol dihydrochloride A solution of 700 mg (2.7 mmol) tert-butyl(S-(R,R)(−)-(1-oxiranyl-2-phenylethyl)-carbamate and 470 mg (3.3 mmol)

3-iso-propylbenzylamine in 10 ml EtOH is heated for 15 h at 50° C. Evaporation of the solvent and purification by column chromatography (silica gel, DCM/MeOH 9:1) afforded 820 mg of [(1S,2R)-1-benzyl-2-hydroxy-3-(3-iso-propyl-benzylamino)-propyl]-carbamic acid tert-butyl ester as a colourless solid. This material is dissolved in 10 ml 4N HCl in dioxane, stirred for 2 h at ambient temperature and all volatiles removed in vacuo to give 643 mg desired compound.

The following compounds can be obtained by a similar procedure:

EXAMPLE 6A (S)—N-[(1S,2R)-1-benzyl-3-(6-bromo-2,2-dimethyl-chroman-4-ylamino)-2-hydroxy-propyl]-2-((S)-1-cyclopropylmethyl-6-oxo-1,7-diaza-spiro[4.4]non-7-yl)-propionamide

MS (EI+): 667, 669 (M+1)

EXAMPLE 6B (S)—N-[(1S,2R)-1-benzyl-2-hydroxy-3-(3-isopropyl-benzylamino)-propyl]-2-((S)-1-cyclopropylmethyl-3-(S)-fluoro-6-oxo-1,7-diaza-spiro-[4.4]non-7-yl)-propionamide

MS (EI+): 579 (M+1)

EXAMPLE 6C (S)—N-[(1S,2R)-1-benzyl-2-hydroxy-3-(3-isopropyl-benzylamino)-propyl]-2-((S)-1-propyl-3-(S)-fluoro-6-oxo-1,7-diaza-spiro-[4.4]non-7-yl)-propionamide

MS (EI+): 567 (M+1)

EXAMPLE 6D (S)—N-{(1S,2R)-1-benzyl-3-[1-(3-bromo-phenyl)-cyclopropylamino]-2-hydroxy-propyl}-2-((S)-1-cyclopropylmethyl-3-(S)-fluoro-6-oxo-1,7-diaza-spiro[4.4]non-7-yl)-propionamide

MS (EI+): 641, 643 (M+1)

EXAMPLE 6E (S)—N-[(1S,2R)-1-benzyl-2-hydroxy-3-(3 -isopropyl-benzylamino)-propyl]-2-[(S)-1-(2-fluoro-ethyl)-6-oxo-1,7-diaza-spiro[4.4]non-7-yl]-propionamide

MS (EI+): 553 (M+1)

EXAMPLE 6F (S)—N-[(1S,2R)-1-benzyl-2-hydroxy-3-(3-isopropyl-benzylamino)-propyl]-2-((S)-1-cyclopropylmethyl-6-oxo-1,7-diaza-spiro[4.4]non-7-yl)-propionamide

MS (EI+): 561 (M+1)

EXAMPLE 7

(S)—N-[(1S,2R)-1-benzyl-2-hydroxy-3-(3-isopropyl-benzylamino)-propyl]-2-((S)-6-oxo-1-prop-2-ynyl-1,7-diaza-spiro-(S)-[4.4]non-7-yl)-propionamide This compound can be prepared as the compound of Example 6, but starting from 2-(6-oxo-1-prop-2-ynyl-1,7-diaza-spiro-(S)-[4.4]non-7-yl)-propionic acid methyl ester instead of 2-(S)-(1-isobutyl-6-oxo-1,7-diaza-spiro-(S)-[4.4]non-7-yl)-propionic acid methyl ester.

The starting material can be prepared as follows:

7a) 2-(S)-(6-oxo-1-prop-2-ynyl-1,7-diaza-spiro(S)-[4.4]non-7-yl)-propionic acid methyl ester 163 mg (0.5 mmol) 7-(1-methoxycarbonyl-(S)-ethyl)-6-oxo-1,7-diaza-spiro-(S)-[4.4]nonane-1-carboxylic acid tert-butyl ester are dissolved in 1.5 mL 4N HCl in dioxane and stirred for 3 h at room temperature. The reaction mixture is evaporated, the residue taken up in 15 mL ethanol/toluene 1:2 and evaporated (twice), to yield 2-(S)-(6-oxo-1,7-diaza-spiro-(S)-[4.4]non-7-yl)-propionic acid methyl ester hydrochloride, which is dissolved in 10 mL DMF, treated with 815 mg (5 eq.) cesium carbonate and 0.048 mL (1.25 eq) prop-2-ynyl bromide. The reaction mixture is stirred at room temperature for 18 h, then extracted (AcOEt/water), washed with brine and the combined organic fractions evaporated. The residue is column chromatographed (silica gel, TBME) to yield 78 mg desired product.

MS (EI+): 265 (M+1)

EXAMPLE 8

(S)—N-[(1S,2R)-1-benzyl-2-hydroxy-3-(3-isopropylbenzylamino)propyl]-2-((S)-6-oxo-1-(2,2,3,3-tetratritiopropyl)-1,7-diaza-spiro[4.4]non-7-yl)-propionamide (S)—N-[(1S,2R)-1-benzyl-2-hydroxy-3-(3-isopropyl-benzylamino)-propyl]-2-((S)-6-oxo-1-prop-2-ynyl-1,7-diaza-spiro-(S)-[4.4]non-7-yl)-propionamide was reduced under 0.9 atmosphere tritium gas on 10% Pd/C for 2 h. The desired compound was obtained after HPLC purification of the reaction mixture (column: Nucleosil 100-5 C18 HD, 5 μm, 250×4.9 mm; eluent: H$_2$O/MeCN and 0.1% trifluoroacetic acid; gradient: 9:1 to 1:1 over 20 minutes) and formulation in ethanol to a final concentration of 9.9 microgram/mL (specific activity 68.6 MBq/mL).

HPLC: RT=12.87 min
ME (ES+): 557 (M+1)

EXAMPLE 9

In Vitro Autoradiography

The tissue of interest is cut in 10 micrometer thick slices for receptor autoradiography with a microtome cryostat and thaw-mounted on silane-coated microscope slides (Vectabond). Sections are air-dried. Preincubation in buffer (50 mM Tris pH 7.4; 2 mM EGTA, 5 mM MgCl2, 0.1 mM bacitracin, 0.2% bovine serum albumine) is for 10 min at air temperature. Ligand binding is done for 1 hr at room temperature in buffer supplemented with 10 nM tritiated compound (specific activity 3.8 TBq/mmol). Non-specific binding is determined in the presence of 10 microM cold compound. Three consecutive washes in buffer and distilled c) water are followed by air-drying and autoradiography (exposure to Biomax MR film (Eastman Kodak Company) for 4 weeks).

EXAMPLE 10

Ex Vivo Autoradiography

The tritiated compound is administered e.g. i.v. with an appropriate formulation, the animal sacrificed at the time point of desired observation, and the tissue of interest is analyzed for instance as described in Example 9.

The invention claimed is:

1. A compound of the formula

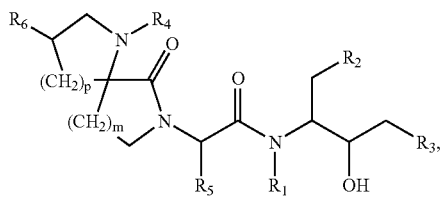

I wherein
$R_1$ is hydrogen or $(C_{1-4})$alkyl,
$R_2$ is optionally substituted $(C_{1-8})$alkyl, $(C_{3-7})$cycloalkyl, $(C_{3-7})$cycloalkyl$(C_{1-4})$alkyl, aryl or heteroaryl,
$R_3$ is —$CH(R_e)C(=O)N(R_a)R_b$ or —$(CH_2)_k N(R_c)R_d$, wherein
k is 0, 1 or 2,
$R_a$, $R_b$, $R_c$ and $R_d$, independently, are hydrogen or an optionally substituted $(C_{1-8})$alkyl, $(C_{5-9})$bicycloalkyl, $(C_{3-7})$cycloalkyl, $(C_{3-7})$cycloalkyl$(C_{1-4})$alkyl, aryl, aryl$(C_{1-4})$alkyl, heteroaryl, heteroaryl$(C_{1-4})$alkyl, 4-chromanyl, 1,2,3,4-tetrahydro-quinolin-4-yl, 1,2,3,4-tetrahydro-naphthalen-1-yl, thiochroman-4-yl-1,1-dioxide, 4-isochromanyl, 1,2,3,4-tetrahydro-isoquinolin-4-yl, thioisochroman-4-yl-1,1-dioxide, 1,1-dioxo-1,2,3,4-tetrahydro-1 lambda*6*-benzo[e][1,2]thiazin-4-yl, 1,1-dioxo-3,4-dihydro-1H-1lambda*6*-benzo[c][1,2]oxathiin-4-yl, 2,2-dioxo-1,2,3,4-tetrahydro-2lambda*6*-benzo[c][1,2]thiazin-4-yl or 2,2-dioxo-3,4-dihydro-2H-2lambda*6*-benzo[e][1,2]oxa-thiin-4-yl group, or
$R_a$ and $R_b$, or $R_c$ and $R_d$, together with the nitrogen to which they are attached, form an optionally substituted pyrrolidinyl, piperidinyl, morpholinyl or piperazinyl group, and
$R_e$ is $(C_{1-8})$alkyl, $(C_{1-4})$alkoxy$(C_{1-4})$alkyl, $(C_{3-7})$cycloalkyl or $(C_{3-7})$cycloalkyl$(C_{1-4})$alkyl,
$R_4$ is hydrogen or an optionally substituted $(C_{1-8})$alkyl, $(C_{1-4})$alkoxy$(C_{1-4})$alkyl, $(C_{3-7})$cycloalkyl, $(C_{3-7})$cycloalkyl$(C_{1-4})$alkyl, $(C_{2-6})$alkenyl, $(C_{2-6})$alkynyl, $(C_{3-7})$cycloalkoxy$(C_{1-4})$alkyl or aryl group,
$R_5$ is hydrogen or optionally substituted $(C_{1-4})$alkyl,
$R_6$ is hydrogen, hydroxy or halogen, and
m and p, independently, are 1 or 2,
in free base form or in acid addition salt form.

2. A process for the preparation of a compound as defined in claim 1 of the formula I, in free base form or in acid addition salt form, comprising the steps of acylating a compound of the formula

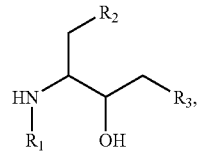

II wherein $R_1$, $R_2$ and $R_3$ are as defined for the formula I, with an acid of the formula

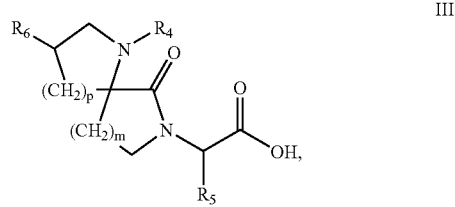

III wherein $R_4$, $R_5$, $R_6$, m and p are as defined for the formula I, or an activated form thereof, and recovering the so obtainable compound of the formula I in free base form or in acid addition salt form.

3. A pharmaceutical composition comprising a compound as claimed in claim 1, in free base form or in pharmaceutically acceptable acid addition salt form, and a pharmaceutical carrier or diluent.

4. The process of claim 2, wherein the activated form thereof of the acid of formula III is an ester or an acid halogenide.

* * * * *